US011369487B2

(12) United States Patent
Cardamone et al.

(10) Patent No.: US 11,369,487 B2
(45) Date of Patent: Jun. 28, 2022

(54) ADJUSTABLE ENDOPROSTHESIS

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Philip Cardamone, Victoria (AU); Manuel Millahn, Munich (DE); Martin Immerz, Gräfelfing (DE)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 194 days.

(21) Appl. No.: 14/891,699

(22) PCT Filed: May 17, 2013

(86) PCT No.: PCT/EP2013/060271
§ 371 (c)(1),
(2) Date: Nov. 17, 2015

(87) PCT Pub. No.: WO2014/183799
PCT Pub. Date: Nov. 20, 2014

(65) Prior Publication Data
US 2016/0106552 A1    Apr. 21, 2016

(51) Int. Cl.
*A61F 2/38* (2006.01)
*A61F 2/46* (2006.01)
(Continued)

(52) U.S. Cl.
CPC ............ *A61F 2/4603* (2013.01); *A61B 90/39* (2016.02); *A61F 2/28* (2013.01); *A61F 2/32* (2013.01);
(Continued)

(58) Field of Classification Search
CPC ............ A61F 2/389; A61F 2002/30546; A61F 2002/30515; A61B 2017/0268
See application file for complete search history.

(56) References Cited

U.S. PATENT DOCUMENTS 4,502,160 A    3/1985  Moore et al.
5,370,693 A *  12/1994 Kelman .............. A61F 2/30724
                                                   623/16.11
(Continued)

FOREIGN PATENT DOCUMENTS

EP    1 642 550     4/2006
GB    2 137 884     10/1984
WO    97/09939      3/1997

OTHER PUBLICATIONS

International Search Report and Written Opinion for International Application No. PCT/EP2013/060271 dated Feb. 21, 2014 (6 pages).

*Primary Examiner* — Megan Y Wolf
(74) *Attorney, Agent, or Firm* — DLA Piper LLP

(57) ABSTRACT

The present application relates to an endoprosthesis including a first member which is connected to a patient's bone; a second member which is adjustably coupled to the first member by a coupling device; wherein the coupling device is configured to generate a movement of the second member relative to the first member. The present application also relates to an artificial joint including such an endoprosthesis and to an endoprosthesis placement system including such an endoprosthesis or artificial joint and a projection device which is configured to project visible light markings, acquired from pre-operational and/or intra-operational patient data, onto the patient and/or the endoprosthesis, thus enabling visible alignment markings of the endoprosthesis to be aligned with respect to projected visible light markings so as to allow a proper adjustment of the endoprosthesis.

9 Claims, 3 Drawing Sheets

(51) Int. Cl.
  *A61F 2/32* (2006.01)
  *A61F 2/28* (2006.01)
  *A61B 90/00* (2016.01)
  *A61F 2/30* (2006.01)

(52) U.S. Cl.
  CPC ............... *A61F 2/38* (2013.01); *A61F 2/389* (2013.01); *A61F 2/4684* (2013.01); *A61B 2090/3937* (2016.02); *A61F 2/3868* (2013.01); *A61F 2002/30507* (2013.01); *A61F 2002/30538* (2013.01); *A61F 2002/30553* (2013.01); *A61F 2002/30556* (2013.01)

(56) References Cited

U.S. PATENT DOCUMENTS

| | | |
|---|---|---|
| 5,413,604 A | 5/1995 | Hodge |
| 5,609,645 A | 3/1997 | Vinciguerra |
| 5,733,292 A * | 3/1998 | Gustilo ............... A61B 17/025 |
| | | 606/86 R |
| 5,755,802 A | 5/1998 | Gerber |
| 5,876,459 A | 3/1999 | Powell |
| 6,454,806 B1 * | 9/2002 | Cohen ................... A61F 2/4455 |
| | | 623/17.15 |
| 7,601,177 B2 | 10/2009 | Naegerl |
| 2003/0153978 A1 * | 8/2003 | Whiteside ............ A61B 5/1127 |
| | | 623/20.21 |
| 2005/0234555 A1 * | 10/2005 | Sutton .................... A61F 2/442 |
| | | 623/17.15 |
| 2006/0069447 A1 * | 3/2006 | DiSilvestro ............... A61F 2/36 |
| | | 623/23.16 |
| 2009/0222089 A1 * | 9/2009 | Hauri ................... A61B 17/025 |
| | | 623/13.13 |
| 2011/0112650 A1 * | 5/2011 | Masini ..................... A61F 2/34 |
| | | 623/20.15 |
| 2012/0158152 A1 * | 6/2012 | Claypool ................ A61F 2/389 |
| | | 623/20.33 |
| 2013/0066432 A1 * | 3/2013 | Colwell, Jr. ........... A61B 5/103 |
| | | 623/18.11 |

* cited by examiner

ADJUSTABLE ENDOPROSTHESIS

RELATED APPLICATION DATA

This application is a national phase application of International Application No. PCT/EP2013/060271 filed May 17, 2013 and published in the English language.

The present invention relates to an adjustable endoprosthesis comprising a first member, a second member and a coupling device for generating a movement of the second member relative to the first member. The present invention also relates to an artificial joint comprising such an adjustable endoprosthesis and to an endoprosthesis placement system and to a method and/or computer program for placing such an endoprosthesis.

Current endoprosthetic implants as used for total knee replacement or total hip replacement are usually press-fitted to the bone or "glued" to the bone using bone cement. In both cases, the implant's position and orientation is determined by the position and orientation of the surface of the corresponding bones which are machined before the implant is placed.

Due to various possible sources of inaccuracy (for example, bending by the saw blade, movement of the cutting slot and/or misinterpretation of values), the position and orientation of the surface of a machined bone (for example, a bone incision) and therefore the position and orientation of the implant may not match the planned position and orientation. If in particular too much bone material is cut away, there is no way of adjusting the implant to the desired position and orientation. The overuse or underuse of bone cement could also cause the implant to be or become incorrectly placed. An incorrectly placed implant ultimately has a shorter service life due to asymmetric wear on the implant's components.

U.S. Pat. No. 5,876,459 discloses an implantable modular orthopaedic prosthesis comprising three components, wherein the third component can be axially moved relative to the first and second components in order to adjust the effective length of the prosthesis.

However, this prosthesis is not able to compensate for inaccuracies in the position of the surface of a machined bone.

The above problems are overcome by the subject-matter of the present application.

The adjustable endoprosthesis according to the present invention comprises:
a first member which is connected to a patient's bone;
a second member which is adjustably coupled to the first member by means of a coupling device;
wherein the coupling device is configured to generate a movement of the second member relative to the first member.

In other words, the geometry of the endoprosthesis in accordance with the invention, which is defined by a first member and a second member, can be adjusted by actuating a coupling device which movably couples the first and second members of the endoprosthesis. This adjustment allows a surgeon to compensate for any inaccurate machining of a patient's bone to which the endoprosthesis is to be attached, which in turn optimises the outcome of the surgery. In other words, the geometry of the endoprosthesis can be adjusted in order to match an actual position of the implanted endoprosthesis which differs from a planned position. Adjusting the implant after a rigid contact with the bone has been established allows the surgeon to compensate for inaccuracies which may occur during surgery and so helps the surgeon to improve the outcome of the surgery. This in turn increases the average service life of the endoprosthesis inserted by the surgeon.

The term "position" as used in this document encompasses both the spatial orientation and the spatial location of an object.

The movement of the second member relative to the first member can be a translational movement, a rotational movement or also a tilting movement which combines a translational movement and a rotational movement. In general, it is possible to allow six spatial degrees of freedom (three rotational degrees of freedom and three translational degrees of freedom) for a movement of the second member relative to the first member. It is also possible to restrict the relative movement to certain translational and/or rotational degrees of freedom using suitable guides which form part of the coupling device. It is also conceivable for the second member to be divided into at least two sectors which can be moved independently of each other.

The coupling device may comprise at least two coupling sections which can be actuated independently of each other so as to generate a movement of the second member relative to the first member. These coupling sections can be arranged in parallel and/or sequentially in order to couple the second member to the first member of the endoprosthesis. One or more coupling sections (arranged in parallel) could for example be assigned to generate a translational movement of the second member relative to the first member, while one or more other coupling sections which are arranged sequentially with respect to the coupling sections assigned to the translational movement could be assigned to generate a rotational movement of the second member relative to the first member of the endoprosthesis.

Although the coupling device or at least one of its coupling sections could be actuated by the surgeon manually, for example by using manual tools, it is also conceivable for the coupling device or at least one of its coupling sections to be actuated automatically, for example by motors which could be detachably attached to the coupling device or at least one of its coupling sections. It is however also conceivable for such motors to be integrated into the endoprosthesis. In any case, such motors could be actuated by a surgeon or automatically by means of a computer so as to generate a desired movement of the second member relative to the first member in order to obtain a desired geometry of the endoprosthesis.

The coupling device may also be configured such that it in particular comprises means for rigidly fixing the relative position of the first and second members. Once a desired relative position of the first and second members is reached after actuating the coupling device or one or more of its coupling sections, the relative position of the first and second members and therefore also the geometry of the endoprosthesis is fixed so as to obtain a permanent geometry of the endoprosthesis. This could be achieved by suitable fixing means which prevent mechanical parts of the coupling device from moving, such as for example spikes which prevent a screw of the coupling device from rotating. It is also conceivable for a curable substance, such as for example bone cement, to be introduced in cavities between mechanical parts and/or side walls of the first and second members in order to prevent the second member from moving any further relative to the first member. It is in any event preferable to introduce a curing substance or any other suitable filler material into gaps which have formed between the first and second members, once the desired geometry of the endoprosthesis has been obtained.

Although the coupling device is preferably placed substantially between the first and second members of the endoprosthesis, it is in principle also possible to place the coupling device at any other location, even out of the vicinity of the first and second members, as long as the coupling device can generate a relative movement between the first and second members.

The coupling device may provide an elastic coupling between the first member and the second member. An inflatable mechanism could for example be provided substantially between the first and second members, wherein said mechanism can be filled with gas or liquid or even a curable filler material such as bone cement. By arranging one or more such inflatable mechanisms (for example in the form of balloons) between the first and second members, the first and second members could be moved away from each other by inflating the inflatable mechanisms and moved towards each other by deflating the inflatable mechanisms, wherein any translational or rotational movements would be conceivable using this method. Spring mechanisms are another example of an elastic coupling.

The coupling device may also provide an inelastic coupling between the first member and the second member. Screws, eccentrics, bolts, wedges, gearwheels or any other suitable mechanisms could for example be provided in order to inelastically couple the first member and the second member.

The first member may be directly connected, in particular cemented or press-fitted, to the patient's bone. However, it is also conceivable for the first member to be indirectly connected to the patient's bone via another member which is directly connected, in particular cemented or press-fitted, to the patient's bone. In other words, any member of the endoprosthesis in accordance with the invention could be configured such that it can be moved with respect to another member of the endoprosthesis by means of a coupling device.

At least one of the first and second members may comprise connecting means for detachably attaching a trackable reference or comprises a trackable reference.

In navigated surgery, such an embodiment also provides the advantage that the position of the members of the endoprosthesis and therefore also the geometry of the endoprosthesis is known during surgery, which allows a surgeon to adjust the geometry of the endoprosthesis to a desired geometry which promises the best result.

At least one of the first member and the second member may comprise an alignment marking which can be a visible alignment marking. Providing such a marking enables the surgeon to adjust the relative position of the first and second members by aligning the alignment marking with markings provided by a projection device, as described further below.

Another aspect of the present invention relates to an artificial joint, in particular an artificial knee joint or artificial hip joint, comprising at least one endoprosthesis as described above. The artificial joint in accordance with the invention can be adjustable in terms of at least one of its joint components (in a primary knee implant, for example, the tibia component, an insert component and/or the femoral component, wherein other parts are also conceivable for revision implants), wherein an adjustable joint insert component which is positioned substantially between two corresponding joint members is preferred. Corresponding joint members could for example be a cup component and a stem component of an artificial hip joint or a tibial component and a femoral component of an artificial knee joint.

Another aspect of the present invention relates to an endoprosthesis placement system comprising an endoprosthesis or artificial joint as described above and a projection device which is configured to project visible light markings, acquired from patient data and/or geometric endoprosthesis/joint data, onto the patient and/or the endoprosthesis, thus enabling visible alignment markings of the endoprosthesis to be aligned with respect to projected light markings so as to allow a proper adjustment of the endoprosthesis.

A laser or any other suitable light source can project information onto the patient and/or the endoprosthesis which indicates an optimum position/geometry of the endoprosthesis. This allows the surgeon to adjust the endoprosthesis geometry until the visible light markings are aligned with or match the visible alignment markings. However, any other embodiment in which the current position (location and/or orientation) of at least one member of the endoprosthesis is indicated in relation to a desired position is conceivable.

Another aspect of the present invention relates to a method of adjusting an endoprosthesis or artificial joint as described above, the first member of which has already been connected to a patient's bone, said method comprising the steps of:

acquiring data which contain information about the desired position of the endoprosthesis/joint;

acquiring data which contain information about the current position of the endoprosthesis/joint;

acquiring data which contain information about the correlation between the movement of the second member relative to the first member and the actuation of the coupling device, in particular at least one of the coupling sections;

displaying adjustment instructions for aligning the current position with the desired position, based on the acquired data.

In other words, the method according to the present invention chronologically follows the steps of machining a patient's bone and connecting the first member of the endoprosthesis to the patient's bone and is therefore merely directed to an adjustment method which ends once a permanent desired geometry of the endoprosthesis has been obtained.

If, as described above, the coupling device or at least one of its coupling sections is provided with motors, it is also conceivable for a movement of the second member relative to the first member to be generated fully automatically by means of a computer which actuates the motors of the coupling device so as to obtain a desired geometry of the endoprosthesis, wherein data concerning the current geometry of the endoprosthesis could be obtained by means of a tracking system which tracks the position of a tracking reference attached to at least one member of the endoprosthesis and therefore also the position of the at least one member of the endoprosthesis and provides the computer with this positional information.

Another aspect of the present invention relates to a computer program which, when it is running on a computer or is loaded onto a computer, causes the computer to perform a method as described above.

Another aspect of the present invention relates to a computer program storage medium comprising a program as described above.

In the following, preferred embodiments of the present invention are described with the aid of the enclosed figures. The present invention can comprise any of the disclosed features, individually or in any suitable combination.

FIG. 1 shows a typical artificial knee joint comprising a femoral component connected to the patient's femur and a tibial component which is connected to the patient's tibia and comprises a stemmed tibial plate which supports a polyethylene (PE) plastic insert arranged between the tibial component and the femoral component of the artificial knee joint.

The tibial component is formed by the endoprosthesis 1 in accordance with the invention, wherein the stemmed tibial plate forms the first member 2 and the PE insert supported by the tibial plate forms the second member 3.

The femoral component and the stemmed tibial plate are press-fitted or cemented to the femur and tibia, respectively. If the tibia has been machined inaccurately, the surgeon can compensate for these inaccuracies by adjusting the position of the PE insert with respect to the stemmed tibial plate in order to optimise the functionality and minimise the wear characteristics of the joint components.

Figure 1:
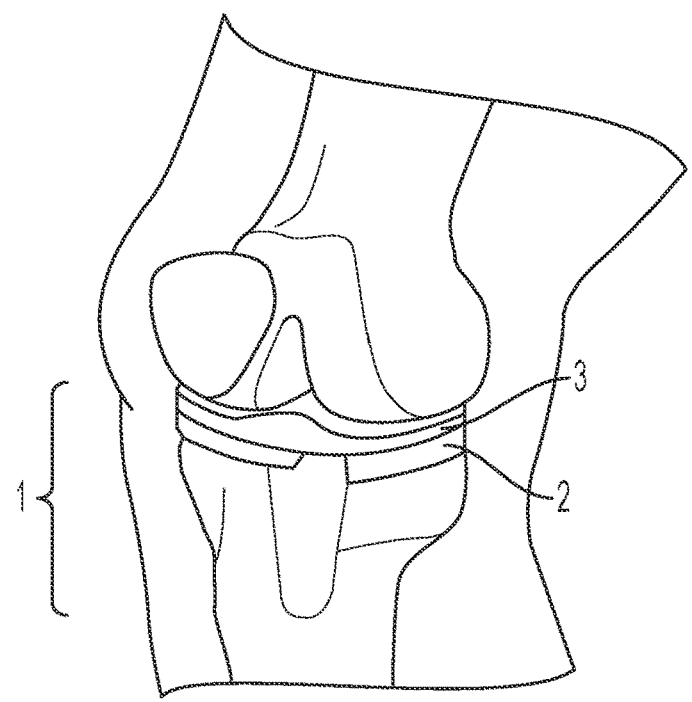
FIG. 1 shows a typical artificial knee joint comprising an endoprosthesis in accordance with the invention.
Figure 2:
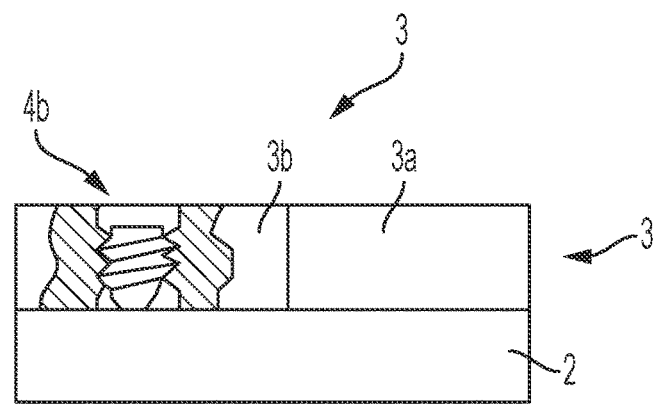
FIG. 2 shows a first example of the endoprosthesis in accordance with the invention.
Figure 2:
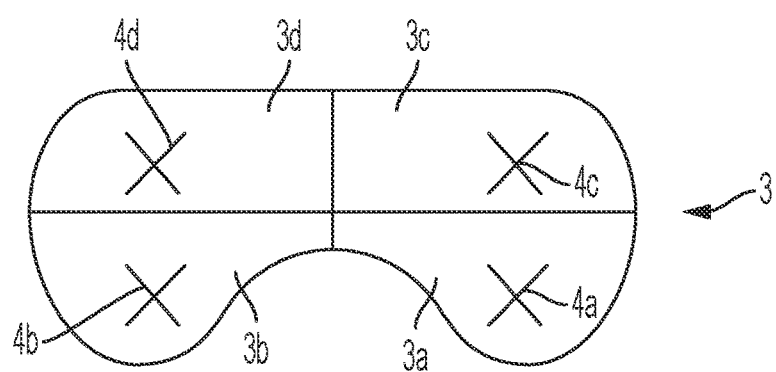

FIG. 2 shows a first embodiment example of the endoprosthesis in accordance with the present invention, wherein the first member 2 is formed by a base section or supporting plate of the artificial knee joint shown in FIG. 1, and the second member 3 is divided into four sectors 3a to 3d, wherein the sectors 3a to 3d are connected to each other and respectively comprise the coupling sections 4a to 4d which together form the coupling device 4 but can be actuated independently of each other. As can be seen in the upper, cross-sectional view in FIG. 2, each coupling section is formed by a setting screw which is inserted into a threaded bore of the respective sector 3a to 3d of the second member 3. Thus, for example, tightening the screws 4a and 4c will cause the second member 3 to tilt to the left, while tightening the screws of the coupling sections 4c and 4d will cause the second member 3 to tilt backwards around a horizontal axis in the lower drawing in FIG. 2. However, it is also conceivable for the sectors 3a to 3d to not be connected to each other and therefore able to be moved independently of each other by actuating the corresponding coupling sections 4a to 4d.

Figure 3:
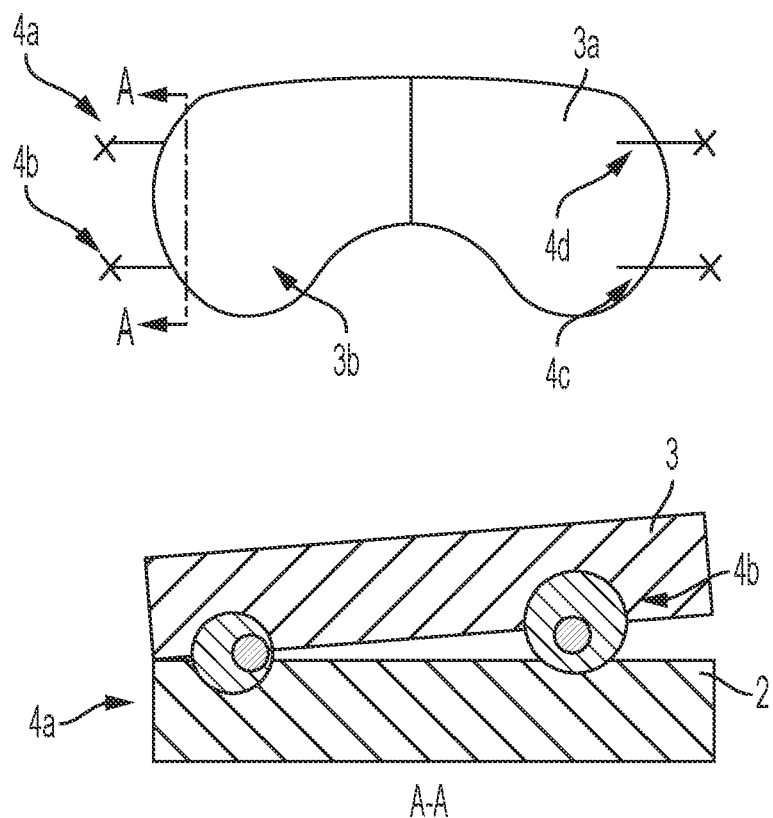
FIG. 3 shows a second example of the endoprosthesis in accordance with the invention, comprising a different coupling mechanism.

FIG. 3 shows a second example of the endoprosthesis in accordance with the present invention, comprising a different type of coupling device 4. This coupling device 4 comprises four extender wheels 4a to 4d, wherein the second member 3 is divided into two sectors 3a and 3b and each sector 3a, 3b can be independently moved by means of two respective extender wheels 4a, 4b or 4c, 4d. As opposed to the setting screws of the coupling sections 4a to 4d of the first example shown in FIG. 2, the extender wheels 4a to 4d according to this embodiment are actuated from the side of the endoprosthesis and not from the top surface.

Figure 4:
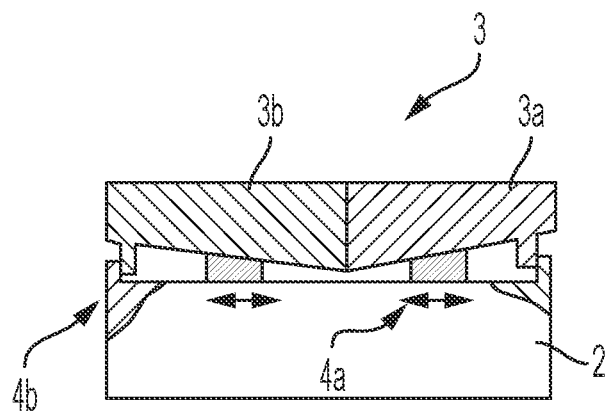
FIG. 4 shows a third example of the endoprosthesis in accordance with the invention, comprising another different coupling mechanism.

FIG. 4 shows a third example of the endoprosthesis in accordance with the present invention, comprising another different coupling device 4 which comprises two coupling sections 4a and 4b which respectively comprise wedges which are arranged between the first member 2 and the corresponding independent sectors 3a and 3b of the second member 3 and can be moved translationally. The wedges of the coupling device 4 can be moved independently of each other in the directions indicated by the arrows in FIG. 4 so as to raise or lower the corresponding sectors 3a and 3b with respect to the first member 2.

Figure 5:
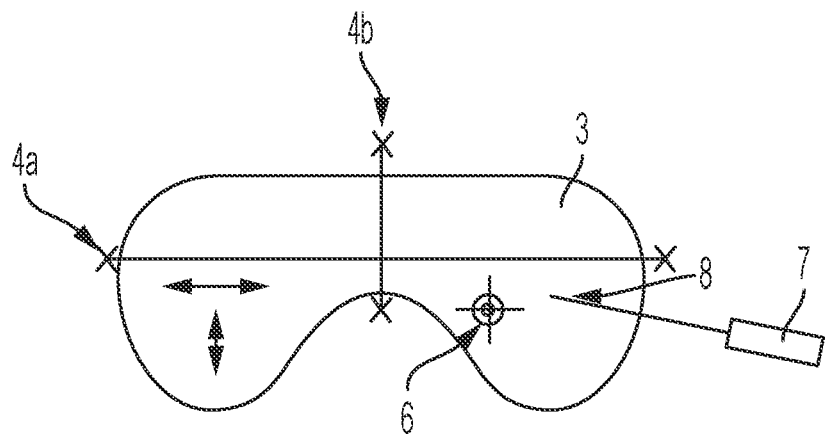
FIG. 5 shows an example of the endoprosthesis in accordance with the invention, comprising alignment markings.

FIG. 5 shows another example of the endoprosthesis in accordance with the present invention, in which two independent screws are provided in order to generate a translational movement of the second member 3 with respect to the subjacent first member 2 (not shown), in the directions indicated by the arrows shown in FIG. 5.

It should be noted that any of the variants and/or configurations of the examples shown in FIGS. 2 to 5 or any other suitable variants and/or configurations of a coupling device and/or second member can be combined sequentially or in parallel so as to move the second member 3 with respect to the first member 2 in a desired manner. The first member 2 shown in FIG. 3 could for example form the second member 3 shown in FIG. 4, and vice versa.

FIG. 5 also shows another feature of the present invention, namely a visible alignment marking 6 which is located on the second member 3 and is to be aligned with a projected marking 8 projected by a laser 7. In the example shown in FIG. 5, the alignment marking 6 does not match the projected marking 8 (distance exaggerated in the figure), hence the surgeon has to move the second member 3 to the right and also upwards, by actuating the screws of the coupling sections 4a and 4b, in order to obtain the desired geometry of the endoprosthesis.

Figure 6:
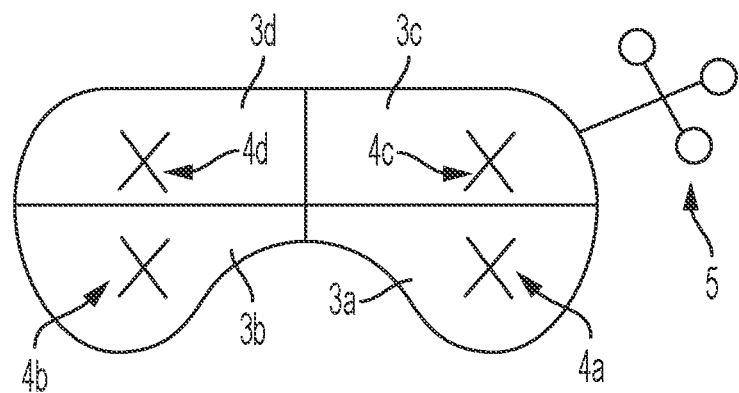
FIG. 6 shows an example of the endoprosthesis in accordance with the invention, comprising a tracking reference.

FIG. 6 shows another example of the endoprosthesis in accordance with the present invention, wherein a tracking reference 5 which is visible to and can be tracked by a surgical tracking system is attached to the second member 3. Since the spatial position of the tracking reference 5 is known to a medical navigation system, the position of the second member 3 and the geometry of the endoprosthesis 1 is also known in real time, such that a surgeon is always aware of the current geometry of the endoprosthesis.

The invention claimed is:

1. A tibial component of an adjustable knee joint endoprosthesis, the tibial component comprising:
   a first member that is connectable to an associated patient's tibia via at least one of a press-fitted connection or a cemented connection;
   a second member configured to cooperate with a femoral component of the adjustable knee joint endoprosthesis, the second member comprising a first portion and a second portion that are independently movable with respect to each other;
   a first coupling section adjustably connecting the first portion to the first member, wherein the first coupling section is configured to cause the first portion to translate, rotate, or a combination thereof relative to the first member when actuated;
   a second coupling section adjustably connecting the second portion to the first member, wherein the second coupling section is configured to cause the second portion to translate, rotate, or a combination thereof relative to the first member when actuated; and
   a tracking reference coupled to at least one of the first member or the second member, wherein the tracking reference is configured to be tracked by a medical navigation system to determine a spatial position of the at least one of the first member or the second member to determine a geometry of the endoprosthesis.

2. The tibial component of an adjustable knee joint endoprosthesis according to claim 1, wherein at least one of the first coupling section or the second coupling section is actuated automatically.

3. The tibial component of an adjustable knee joint endoprosthesis according to claim 1, wherein the first coupling section and the second coupling section provide an inelastic coupling between the first member and the second member.

4. The tibial component of an adjustable knee joint endoprosthesis according to claim 1, wherein at least one of the first member and the second member comprises a visible alignment marking.

5. The tibial component of the adjustable knee joint endoprosthesis according to claim 1, wherein:
the second member further comprises a third portion and a fourth portion;
the first portion, the second portion, the third portion, and the fourth portion are independently movable with respect to each other;
the tibial component further comprises:
a third coupling section adjustably connecting the third portion to the first member; and
a fourth coupling section adjustably connecting the fourth portion to the first member;
the third coupling section is configured to cause the third portion to translate, rotate, or a combination thereof relative to the first member when actuated; and
the fourth coupling section is configured to cause the fourth portion to translate, rotate, or a combination thereof relative to the first member when actuated.

6. The tibial component of the adjustable knee joint endoprosthesis according to claim 1, wherein each of the first coupling section and the second coupling section comprises a fastener.

7. The tibial component of the adjustable knee joint endoprosthesis according to claim 1, wherein each of the first coupling section and the second coupling section comprises a wedge movably positioned between the first member and the second member.

8. The tibial component of the adjustable knee joint endoprosthesis according to claim 1, wherein each of the first coupling section and the second coupling section comprises an eccentric wheel rotatably positioned between the first member and the second member.

9. An endoprosthesis placement system comprising:
a tibial component of an adjustable knee joint endoprosthesis, the tibial component comprising:
a first member that is connectable to an associated patient's tibia via at least one of a press-fitted connection or a cemented connection;
a second member configured to cooperate with a femoral component of the adjustable knee joint endoprosthesis, the second member comprising a first portion and a second portion that are independently movable with respect to each other;
a first coupling section adjustably connecting the first portion to the first member, wherein the first coupling section is configured to cause the first portion to translate, rotate, or a combination thereof relative to the first member when actuated;
a second coupling section adjustably connecting the second portion to the first member, wherein the second coupling section is configured to cause the second portion to translate, rotate, or a combination thereof relative to the first member when actuated; and
a tracking reference coupled to at least one of the first member or the second member, wherein the tracking reference is configured to be tracked by a medical navigation system to determine a spatial position of the at least one of the first member or the second member to determine a geometry of the endoprosthesis; and
a projection device that is configured to project visible light markings, acquired from patient data or geometric endoprosthesis/joint data, onto an associated patient or the endoprosthesis, thereby enabling visible alignment markings of the endoprosthesis to be aligned with respect to the projected visible light markings so as to allow a proper adjustment of the endoprosthesis.

\* \* \* \* \*